United States Patent [19]

Nagaraja et al.

[11] Patent Number: 6,077,516

[45] Date of Patent: *Jun. 20, 2000

[54] LIVE VACCINE AGAINST COLIBACILLOSIS

[75] Inventors: Kakambi V. Nagaraja, St. Paul; Daryll Emery, Hugo, both of Minn.

[73] Assignee: Regents of the University of Minnesota, Minneapolis, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/427,205

[22] Filed: Apr. 24, 1995

Related U.S. Application Data

[62] Division of application No. 07/925,820, Aug. 4, 1992, which is a continuation of application No. 07/647,157, Jan. 29, 1991.

[51] Int. Cl.$^7$ .......................... A61K 39/108; C12P 21/06; C12P 21/04
[52] U.S. Cl. .................... 424/257.1; 435/68.1; 435/69.1; 435/70; 435/71.1; 435/320
[58] Field of Search .......................... 424/257.1; 435/68, 435/70, 69.1, 71.1, 320

[56] References Cited

U.S. PATENT DOCUMENTS

| | | |
|---|---|---|
| 4,337,314 | 6/1982 | Oeschger et al. |
| 4,379,140 | 4/1983 | Jensen ........................................ 424/92 |

OTHER PUBLICATIONS

Emery and Nagaraja, "Development of a Temperature Sensitive Mutant of *E. coli* for the Control of Colibacillosis in Turkeys", 39th North Central Avian Disease Conference (Sep. 21 and 22, 1988).
Emery and Nagaraja, "The Use of Temperature Sensitive Mutants for *Escherichia Coli* for the Control of Colibacillosis in Turkeys", Abstract from Conference of Research Workers in Animal Disease (Nov. 14, 1988).
Baltz and Stonesifer, "Adaptive Response and Enhancement of N–methyl=N$^1$–Nitro–N–Nitrosoguanidine Mutagensis by Chloramphenicol in *Streptomyces fradiae*", *J. of Bact.*, 164, 944–946 (1985).
Sklar, Enhancement of Nitrosoguanidine Mutagenesis by Chloramphenicol in *Escherichia coli* K–12, *J. of Bact.*, 136, 460, 462 (1978).
Adelberg et al., "Optical Conditions For Mutagenesis By N–Methyl–N–Nitoro–N–Nitrosoguanidine In *Escherichia coli* K12," *Biochemical and Biophysical Research Communications*, 18(No. 5–6):788–795 (1965).
Wisseman et al., "Mode of Action of Chloramphenicol," *Journal of Bacteriology*, 67:662–673 (1954).
Friefelder, D.M. "Metagenesis, Mutations and Mutants," *Molecular Biology*, 2$^{nd}$ ed. Jones and Bartlet, 306 (1987).
Cooper et al., "A Temperature Sensitive Nonsense Mutation Affecting the Synthesis of a Major Protein of *Escherichia coli* K12," *Molec. gen. Genet.*, 139:167–178 (1975).
Beckman et al., "Temperature–Sensitive Nonsense Mutations in Essential Genes of *Escherichia coli,*" *Journal of Bacteriology*, 116(3):1336–1342 (1973).
Shiba et al., "A defined mutation in the protein expot gene within the spc ribosomal protein operon of *Escherichia coli* isolation and characterization of a new temperature–sensitive secY mutant," *The MBO Journal*, 3(3):631–635 (1984).
Burke et al., "Immunization Against Turkey Coryza by Colonization with Mutants of *Alcaligenes faecalis,*" *Avian Diseases*, 24(3):726–733 (1980).
Burke et al., "Field Vaccination Trials Against Turkey Coryza Using a Temperature–Sensitive Mutant of *Alcaligenes faecalis,*" *Avian Diseases*, 25(1):96–103 (1980).
Panigraphy et al., "Bacterial coryza in turkeys in Texas," *Poult. Sci.*, 60(1):107–113 (1981).
Houghten et al., "Efficacy in Turkeys in Spray Vaccination with a Temperature–Sensitive Mutant of Bordetella avium (Art Vax™)," *Avian Diseases*, 31(2):309–314 (1986).
Heeg et al., "Development of a Live Vaccine to Prevent Air Sacculities in Chickens," *Abstracts of the 90$^{th}$ Annual Meeting of the American Society of Microbiology*, E–4 (1990).
Declaration of Daryll A. Emery.
Rutten et al, "The Antimitogenic Effect of Connamaldehyde is Due to a Transient Growth Inhibitor" *Mut. Res* 201:97–105, 1980.
Mitchel et al "Inducible Error–Prone Repair in Yeast" *Mut. Res.* 159:31–39, 1986.
Emery et al "Development of a Temperature Sensitive Mutant of *E. coli* for Control of Colibioceilosis in Turkeys" Abstract, 39$^{th}$ NCAD.

*Primary Examiner*—James C. Housel
*Assistant Examiner*—Rodney P. Swartz
*Attorney, Agent, or Firm*—Merchant & Gould P.C.

[57] ABSTRACT

A vaccine for the immunization of domestic fowl, such as turkeys and chickens, against *E. coli* infections (Colibacillosis) is disclosed which contains an effective amount of a live temperature sensitive mutant of *E. coli* dispersed in a physiologically acceptable, non-toxic liquid vehicle. The *E. coli* mutant disclosed exhibits growth at 32° C. but not at 41° C. and has a reversion frequency of less than about $1 \times 10^{-8}$.

3 Claims, 2 Drawing Sheets

LIVE VACCINE AGAINST COLIBACILLOSIS

This is a division, of application Ser. No. 07/925,820, filed Aug. 4, 1992, which is a Continuation of application Ser. No. 07/647,157, filed Jan. 29, 1991, now abandoned.

FIELD OF THE INVENTION

The present invention relates to a live mutant *E. coli* vaccine.

BACKGROUND OF THE INVENTION

Infections with *Escherichia coli*, commonly referred to as colibacillosis, are a major cause of death among birds in the poultry industry. Outbreaks of colibacillosis have been reported in ducks, chickens, and turkeys.

*E. coli* is subdivided into serological groups based on the antigenic differences of the lipopolysaccharide somatic O, flagellar H and K capsular antigens. More than 170 different O antigens of *E. coli* have been identified by specific agglutination reactions. In addition, approximately 56 H antigens and over 80 K antigens have been described. Relatively few serological groups of *E. coli* have been identified in disease outbreaks of colibacillosis. The serological groups usually responsible are 01a:K1; 02a:K1; and 078:K80. Other serological groups less frequently incriminated in disease outbreaks are 03, 06, 08, 011, 015, 022, 055, 074, 088, 095, and 0109.

*E. coli* is a normal inhabitant of the intestinal tract of most mammals and birds. Birds are continuously exposed to *E. coli* through contaminated feces, water, feed and other aspects of their environment. Virulent and avirulent strains of *E. coli* shed into the poultry house environment can survive in dust for periods exceeding 32 weeks in an atmosphere of low humidity. The high concentration of *E. coli* in the poultry house environment, together with the ability of these bacteria to survive for long periods of time, results in the continuous exposure of birds to potential pathogens.

*E. coli* is an opportunistic organism causing disease in an already predisposed or immunosuppressed host. Birds become extremely susceptible to respiratory infections of *E. coli* during primary infections of New castle disease, Mycoplasmosis and Infectious bronchitis. The respiratory tract is the predominant route of exposure leading to clinical infections of *E. coli*. This is primarily due to inhalation of contaminated dust during periods of low humidity, crowding of birds, and reduced ventilation with excess accumulation of ammonia.

Two forms of *E. coli* disease are recognized in the poultry industry (i.e., systemic colibacillosis and enteric colibacillosis). However, poultry are normally only affected by the systemic form of colibacillosis, typically after a previous respiratory disease. In systemic colibacillosis, the invading organism passes through the mucosa of the alimentary or respiratory tract and enters the blood stream. This invasion may result in a generalized infection (colisepticaemia) or localized infection.

Respiratory distress and sneezing associated with lesions of the lower respiratory tract are characteristic of colibacillosis. Most deaths occur during the first five days of the disease. The disease has been associated with a number of pathological conditions: Fibrinous pericarditis; perihepatitis; coligranuloma; salpingitis; synovitis; and air-sacculitis.

The control of many bacterial diseases in chickens and turkeys is often accomplished by immunologic intervention with protective vaccines. Both live and inactivated vaccines have been employed in chicken and turkey populations. Attenuated viable organisms have been employed for inducing protection against *Mycoplasma gallisepticum*, *Pasteurella multocida*, and *Alcaligenes faecalis* [H. E. Adler et al., *Am. J. Vet. Res.*, 21, 482–485 (1960); H. E. Adler et al., *Avian Dis.*, 14, 763–769 (1970); I. Hertman et al., *Avian Dis.*, 24, 863–869 (1979); D. S. Burke et al., *Avian Dis.*, 24, 726–733 (1980); A. Michael et al., *Avian Dis.*, 24, 870–877 (1979); A. Michael et al., *Avian Dis.*, 24, 878–884 (1979); J. T. Rice et al., *Abstr. in Poultry Sci.*, 55, 1605 (1976); S. R. Coates et al., *Poultry Sci.*, 56, 273–276 (1977)]. See also U.S. Pat. No. 4,379,140. These attenuated live vaccines have been successfully applied in the drinking water and protect turkeys against intravenous challenge with the homologous serotypes. Inactivated vaccines or bacterins utilizing various adjuvants have been very successful, particularly against such diseases as fowl cholera (*P. multocida*) and infectious coryza (*H. paragallinarum*). Monovalent bacterins have been shown to protect against homologous challenge and possibly against heterologous antigens as well [S. R. Coates et al., supra (1977); B. W. Bierer, *Poultry Sci.*, 48, 633–666 (1969); A. Michael et al., *Refuah Vet.*, 33, 117–121 (1976)]. Inactivated *E. coli* vaccines have been shown to provide protection against systemic challenge, but failed to protect when birds were challenged orally or by the respiratory aerosol method [J. R. Deb et al., *Res. Vet. Sci.*, 24, 308–313 (1978); L. H. Arp, *Avian Dis.*, 24, 808–814 (1980); A. Zanella et al., in *Developments in Biological Standardization*, Y. Moreau and W. Hennessen, eds., S. Krager, Basel., Vol. 51, pp. 19–32 (1982); J. R. Deb et al., *Res. Vet. Sci.*, 20, 131–138 (1976)].

Immunologic intervention with protective vaccines for the control of colibacillosis in the avian species has met with limited success. The problems in controlling this disease lie partly in determining the factors affecting virulence of strains, colonization, invasiveness, and toxin production [M. M. Levine, in *Bacterial Vaccines*, R. Germanier, ed., Academic Press, Orlando, Fla., pp. 187–235 (1984); M. M. Levine et al., *Microbic. Rev.*, 47, 510–550 (1983)].

An oral or aerosol vaccine against colibacillosis has several advantages over parental vaccines, including the ease of administration and the lack of adverse side reactions. The ability to colonize the upper nasal mucosa would profoundly influence the immunogenic efficiency of an aerosol vaccine. Since the respiratory tract is the primary entrance site for these pathogenic *E. coli* organisms, direct stimulation of local secretory antibodies at the portal of entry can enhance immunization against infection in several ways: it would prevent adhesion and colonization of infecting organisms; neutralize toxins; and may have a bactericidal effect, thus inhibiting the systemic entry of *E. coli*. See S. H. Parry et al., in *The Virulence of Escherichia coli*, M. Sussman, ed., The Society for General Microbiology, Academic Press, pp. 79–153 (1985); J. H. Darbyshire, in *Avian Immunology*, A. Toivanen and P. Toivanen, eds., CRC Press, Inc., Vol. 11, pp. 129–161 (1987); J. H. Darbyshire et al., *Res. Vet. Sci.*, 38, 14–21 (1985); J. B. Kaper et al., *Vaccine*, 6, 197–199 (1987); M. M. Levine et al., *Infect. Immun.*, 23, 729–736 (1979)]. A greater local immune response can be induced using live vaccines as opposed to an inactivated, killed vaccine. This may be due to antigens present on live bacteria that may be absent or altered on inactivated, killed bacteria. However, live vaccines employing mutant strains of bacteria are subject to reversion, thereby resulting in loss of the desired immunologic characteristic.

Because of modern high-density confinement rearing practices and the ubiquitous nature of colibacillosis, it has been extremely difficult to control. The control and prevention of avian colibacillosis has, to a large extent, depended upon proper management practices such as use of pelletized feed, free of fecal contamination; the control of rodent populations; proper ventilation; the use of noncontaminated drinking water; and the control of fecal contamination of hatching eggs. Accordingly, there is a need for a stable live vaccine effective to immunize domestic fowl such as turkeys and chickens against colibacillosis.

SUMMARY OF THE INVENTION

The present invention is directed to a vaccine which is effective to immunize domestic fowl such as turkeys, chickens, and ducks against colibacillosis. The vaccine comprises an effective amount of a stable live temperature sensitive mutant of Escherichia coli dispersed in a physiologically acceptable non-toxic vehicle. The mutant bacteria is characterized by growth at 32° C. but not at 41° C. and a reversion frequency of less than about $1\times10^{-8}$, and most preferably less than $1\times10^{-9}$. Intranasal vaccination of turkeys with a single dose of a suspension of about $10^7$ CFU (colony forming units) of the temperature sensitive mutant in 0.1 ml normal saline provides 100% protection against infection due to a virulent strain of E. coli.

Preferred embodiments of the invention employ temperature sensitive mutants of E. coli serotypes 078, 01a, and 02a. A preferred vaccine includes suspending the temperature sensitive mutant in a physiologically acceptable non-toxic liquid vehicle to yield an oral or aerosol vaccine. A preferred vaccine is capable of colonizing the upper nasal mucosa of a domestic fowl for at least 20 days post inoculation.

The present invention further provides a method for obtaining a temperature sensitive mutant of Escherichia coli capable of colonizing the nasal mucosa of a domestic fowl, such as a turkey, chicken, or duck. The preferred method includes the steps of (a) treating a culture of Escherichia coli with amounts of a mutagen and a protein synthesis inhibitor, sufficient to maximize mutation and minimize reversion frequency; and (b) selecting culture mutants exhibiting growth at 32° C. but not at 41° C. and having a reversion frequency of less than $1\times10^{-8}$, and preferably less than $1\times10^{-9}$. Preferably, the culture is treated with about 1000 $\mu$g/ml of the mutagen N-methyl-N-nitro-N-nitrosoguanidine.

DETAILED DESCRIPTION OF THE INVENTION

The immunogenic bacteria employed as the active component of the present vaccines is a stable live temperature sensitive mutant of Escherichia coli exhibiting the following properties: (1) inhibited growth at the internal body temperature of poultry (41° C.); (2) avirulence to poultry when administered intravenously; and (3) colonizing ability for extended periods of time at the cooler tissues of the upper nasal mucosa of poultry. The ts-mutant produced according to the present invention was able to grow at 32° C. and was unable to grow at 41° C.

While E. coli is a normal inhabitant of the intestinal tract of most mammals and birds, most diseases and particularly colibacillosis in poultry is associated with relatively few serological groups--for example, 01a, 02a, and 078. Serotype 078 is the serotype isolated most frequently in outbreaks of colibacillosis. It will be understood that the parent strain of E. coli used to select a mutant for a vaccine of the present invention will be one of the virulent colibacillosis producing strains. As used herein, the term "stable" describes mutant resistance to reversion of one or more of the above selected mutation characteristics. In general, "mutation" refers to a sudden heritable change in the phenotype of an organism which can be spontaneous or induced by known mutagenic agents, including radiation and various chemicals. Among the useful chemical mutagens for the present invention are N-methyl-N-nitro-N-nitrosoguanidine fg(MNNG), ethyl methane sulfonate (EMS), nitrous acid, or the like. A preferred mutagen is MNNG used in amounts from about 10 $\mu$g/ml to 1000 $\mu$g/ml, most preferably in an amount of about 1000 $\mu$g/ml.

According to the present invention, in order to maximize mutagenesis and minimize reversion of the mutants obtained, a protein synthesis inhibitor is employed, in addition to the above-mentioned mutagen. Protein synthesis inhibitors useful in the present invention include chloramphenicol, actinomycin, Spectinomycin, Lincomycin, Erythromysin, or the like. A preferred protein synthesis inhibitor is chloramphenicol.

In a preferred embodiment, to maximize mutation and minimize reversion, amounts of chloramphenicol from about 10 to 50 $\mu$g/ml, preferably 25 $\mu$g/ml to 50 $\mu$g/ml , and most preferably in an amount of about 25 $\mu$g/ml are used. The use of a known mutant such as MNNG, in combination with chloramphenicol, unexpectedly produces mutants with reversion frequencies of less than $1\times10^{-9}$. These mutants have been observed to remain stable for up to 32 passages or subcultures.

To use the ts-mutant of the present invention as a vaccine agent, cells of the selected mutant are combined with a suitable physiologically acceptable non-toxic liquid vehicle such as a saline solution having a concentration of up to at least 0.85%. The amount of cells included in a given unit dosage form of vaccine can vary widely, and depends upon factors such as the age, weight and physical condition of the subject considered for vaccination. Such factors can be readily determined by the clinician or veterinarian employing animal models or other test systems which are well known to the art. A unit dose of the vaccine can be administered parenterally, e.g., by subcutaneous or by intramuscular injection; however, oral or aerosol delivery is preferred. The preferred vaccine may be administered by mixing the ts-mutant strain in the birds drinking water and making the water available to the birds for 4 to 24 hours. Alternatively, the vaccine may be administered intranasally by dropping the nares or as an aerosol. Exemplary titers of ts-E. coli mutant cells in an effective vaccine will range from about $1\times10^6$ to $1\times10^{11}$ colony forming units/ml, preferably from about $1\times10^7$ to $1\times10^{10}$ CFU/ml.

As described in the Examples below, when the ts-E. coli mutant vaccine was administered to turkeys intravenously, no mortality was exhibited, unlike turkeys given the parent virulent non-mutant by the same route. All turkeys given the parent non-mutant died within one week post inoculation.

Extensive colonization of the nasal mucosa was seen with the ts-E. coli mutant strain. There was minimal colonization of the mutant in the trachea. Colonization of the upper nasal mucosa with the mutant lasted 20 days. Turkeys challenged intranasally with virulent E. coli 078 showed a dramatic decrease in the ability of this pathogenic serotype to colonize the nasal mucosa.

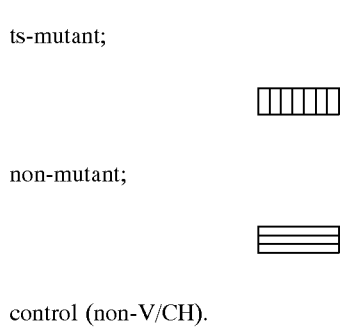

ts-mutant;

non-mutant;

control (non-V/CH).

Figure 2:
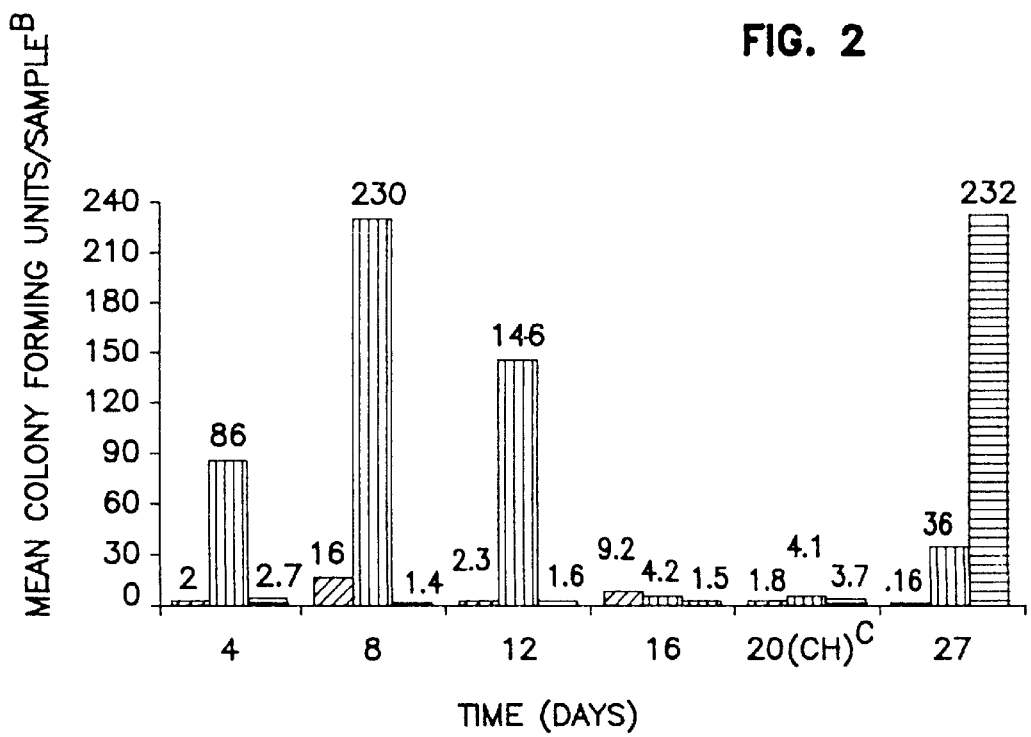

FIG. 2 is a graphic description of tracheal colonization of temperature sensitive mutant, non-mutant *E. coli* 078 and control (non-vaccinated/challenged). The mutant and non-mutant groups were intranasally inoculated at two weeks of age. The control was non-inoculated/challenged. Each sampling time represents the mean colony forming units/group taken intranasally at four-day intervals. Twenty days post inoculation, all groups were challenged intranasally with $2\times10^6$ CFU/bird with a nalidixic acid resistant strain of *E. coli* 078

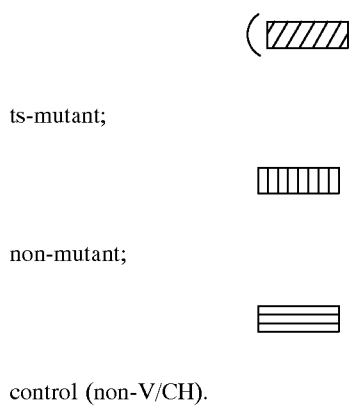

ts-mutant;

non-mutant;

control (non-V/CH).

Figure 3:
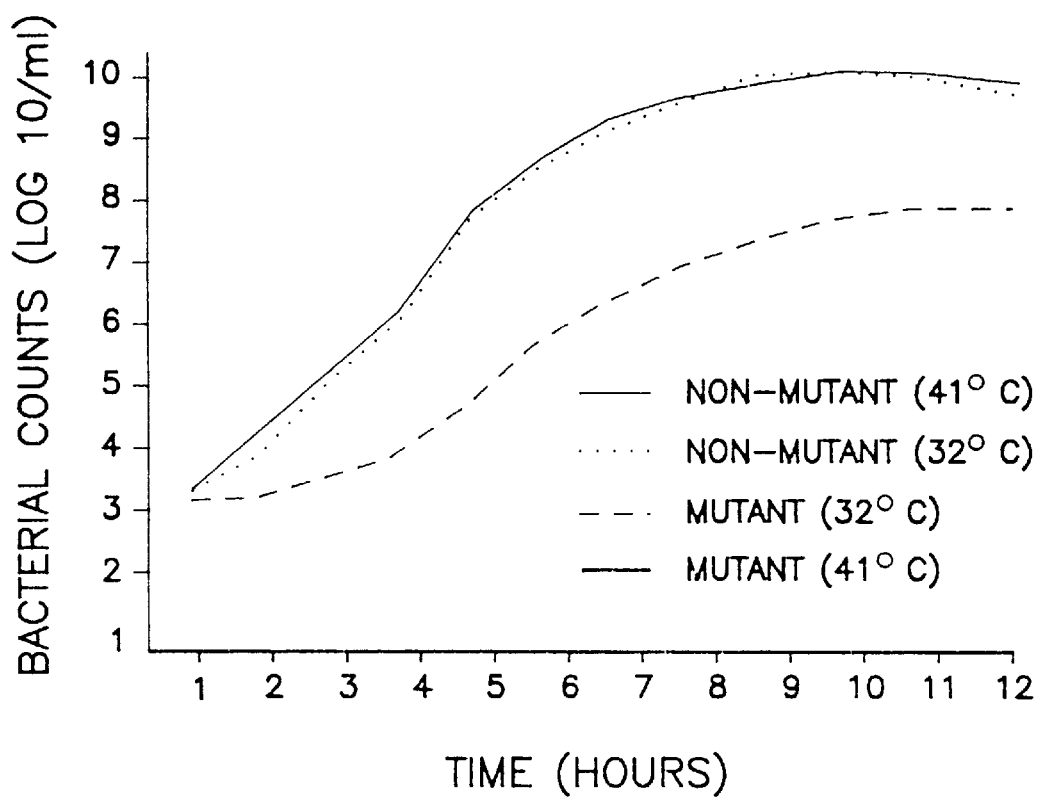

FIG. 3 is a bacterial growth curve of mutant and non-mutant *E. coli* 078 at 32° C. and 41° C.

The following non-limiting Examples are illustrative of the present invention.

EXAMPLE 1

Live Mutant 078 *E. coli* Vaccine

Preparation And Evaluation of Efficacy in Turkeys

A. Bacteria. A field isolate of *E. coli* (serotype 078:K80) was used for the mutagenesis. For challenge, a parent virulent non-mutant strain of the same serotype was used, but was nalidixic acid (Sigma Chemical Co., St. Louis, Mo.) resistant. Bacteria resistant to nalidixic acid were obtained by spreading 1 ml of a 12 hour broth culture, containing $10^8$ viable organisms per ml over the surface of a MacConkey agar (Difco) plate containing 500 ng/ml nalidixic acid. The plates were incubated at 37° C. for 24 hours and colonies that grew were cloned by plating on MacConkey's agar containing 100 ng/ml nalidixic acid.

B. Mutation and selection of ts-mutant. The induction of the ts-mutant of *E. coli* was done by first establishing a culture in exponential growth phase. One milliliter of a 12 hour culture, grown at 37° C. in triptic soy broth (TSB) was transferred to 20 ml TSB prewarmed to 37° C. with continuous shaking for 5 hours. The culture was centrifuged at 15,000×g for 10 minutes and resuspended in 20 ml of TSB (pH 7.2) containing a final concentration of 1000 μg/ml of N-methyl-N-nitro-N-nitrosoguanidine (Sigma), prewarmed to 32° C. The mixture was then incubated with continuous shaking for 5 minutes at 32° C., at which time chloramphenicol (Sigma) was added to give a concentration of 25 μg/ml. The mixture was then incubated for an additional 15 minutes. After this period of incubation, an equal volume of cold (4° C.) phosphate buffered saline (PBS) pH 7.2 was added to the mixture and centrifuged at 15,000×g for 10 minutes. This step was repeated two more times with an equal volume of PBS to remove all residual MNNG.

Bacteria exposed to MNNG were serially diluted 10-fold and plated onto MacConkey agar plates, incubated at 32° C. for 48 hours. Plates having 50–150 colonies were replica plated using a replicate colony transfer pad (FMC Bio Products, Rockland, Ma.) onto two other MacConkey agar plates, one was incubated at 32° C. and the other at 41° C. Mutants were selected based on smaller colony morphology than the parental strain and inhibited growth at 41° C.

C. Reversion frequency and rate of growth. The reversion frequency and rate of growth of selected ts-mutants at permissive and restricted temperatures were determined and compared to that of the non-parent mutant *E. coli*. The reversion frequency was calculated by dividing the number of colony forming units at 41° C. by the number of colony forming units at 32° C. (CFU at 41° C./CFU at 32° C.). Stability against reversion was tested by culturing 12 successive 48 hour back passages in TSB at permissive and restricted temperatures.

Eight ts-mutants were selected after screening several thousand colonies. Mutants were selected based on smaller colony morphology than the parent strain and inhibited growth at 41° C. The reversion frequency of these mutants ranged from $10^{-3}$ to $10^{-9}$, as indicated in Table 1 below.

TABLE 1

REVERSION FREQUENCY OF SELECTED TS-MUTANTS

| MUTANT | CFU AFTER 12, 48 HR BACK PASSAGES | | REVERSION FREQUENCY *CFU AT |
|---|---|---|---|
| | 41C | 32C | 41C/CFU AT 32C |
| ts-1 | $2.2 \times 10^6$ | $5.0 \times 10^9$ | $0.4 \times 10^{-3}$ |
| ts-2 | $2.0 \times 10^1$ | $2.2 \times 10^{10}$ | $0.9 \times 10^{-9}$ |
| ts-3 | $1.6 \times 10^5$ | $1.3 \times 10^9$ | $1.2 \times 10^{-4}$ |
| ts-4 | $2.0 \times 10^4$ | $3.7 \times 10^9$ | $0.5 \times 10^{-5}$ |
| ts-5 | $8.1 \times 10^2$ | $5.3 \times 10^{10}$ | $1.5 \times 10^{-8}$ |
| ts-6 | $1.0 \times 10^6$ | $8.3 \times 10^9$ | $0.1 \times 10^{-3}$ |

TABLE 1-continued

REVERSION FREQUENCY OF SELECTED TS-MUTANTS

| MUTANT | CFU AFTER 12, 48 HR BACK PASSAGES | | REVERSION FREQUENCY *CFU AT |
|---|---|---|---|
| | 41C | 32C | 41C/CFU AT 32C |
| ts-7 | $1.5 \times 10^2$ | $6.1 \times 10^{10}$ | $0.2 \times 10^{-8}$ |
| ts-8 | $8.5 \times 10^3$ | $9.1 \times 10^9$ | $0.9 \times 10^{-6}$ |

*CFU = COLONY FORMING UNITS

The mutant with the lower reversion frequency of $10^{-9}$ was selected as the vaccine strain to be evaluated. The strain has been deposited with the American Type Culture Collection, Rockville, Md., (ATCC No. 55141, deposit date Jan. 21, 1991). All other mutants were lyophilized and stored for future evaluation.

The mutant with the lowest reversion frequency was selected and its rate of growth at 32° C. and 41° C. was compared to the parent non-mutant *E. coli*. The parent non-mutant and mutant *E. coli* were inoculated into TSB pre-warmed to 32° C. (mutant) and 41° C. (non-mutant) for an incubation period of 6 hours. The cultures were adjusted to 90% T at a wavelength of 540 nm. One milliliter of each culture was transferred to 20 ml TSB. Both the mutant and non-mutant were incubated at 41° C. and 32° C. Standard plated counts were done in duplicate for a period of 12 hours. The growth curve of the mutant at 32° C. and 41° C. was determined and compared to that of the non-mutant E. coli (see Table 2 below).

TABLE 2

TWELVE HOUR GROWTH CURVE OF MUTANT AND NON-MUTANT *E. COLI* 078 INCUBATED AT 32 C. AND 41 C.[A]

AVERAGE OF DUPLICATE PLATE COUNTS

| HOUR | MUTANT 32° C. | MUTANT 41° C. | NON-MUTANT 32° C. | NON-MUTANT 41° C. |
|---|---|---|---|---|
| 1 | $17 \times 10^3$ | 0 | $18 \times 10^3$ | $17 \times 10^3$ |
| 2 | $19 \times 10^3$ | 0 | $20 \times 10^4$ | $18 \times 10^4$ |
| 3 | $49 \times 10^3$ | 0 | $50 \times 10^5$ | $42 \times 10^5$ |
| 4 | $80 \times 10^3$ | 0 | $56 \times 10^6$ | $65 \times 10^6$ |
| 5 | $22 \times 10^5$ | 0 | $24 \times 10^7$ | $51 \times 10^7$ |
| 6 | $52 \times 10^5$ | 0 | $18 \times 10^8$ | $15 \times 10^8$ |
| 7 | $49 \times 10^6$ | 0 | $10 \times 10^9$ | $14 \times 10^9$ |
| 8 | $20 \times 10^7$ | 0 | $52 \times 10^9$ | $48 \times 10^9$ |
| 9 | $40 \times 10^7$ | 0 | $26 \times 10^{10}$ | $25 \times 10^{10}$ |
| 10 | $78 \times 10^7$ | 0 | $33 \times 10^{10}$ | $22 \times 10^{10}$ |
| 11 | $97 \times 10^7$ | 0 | $26 \times 10^{10}$ | $34 \times 10^{10}$ |
| 12 | $14 \times 10^8$ | 0 | $12 \times 10^{10}$ | $30 \times 10^{10}$ |

[A]SAMPLES WERE TAKEN FROM EACH GROUP AT ONE HOUR INTERVALS AND PLATED IN DUPLICATE ON EOSIN METHYLENE BLUE AGAR

The growth curve of the mutant strain at 32° C. and 41° C. compared to that of the parent non-mutant *E. coli* is shown in FIG. 3. As indicated in FIG. 3, the mutant was able to grow at 32° C. but unable to grow at 41° C.

The parent non-mutant grew equally well at both temperatures. There was a three-log difference in growth of the mutant at 32° C. compared to that of the parent non-mutant at 32° C. and 41° C. for the duration of the growth curve. A mutant with a reduced growth rate able to colonize the upper nasal mucosa was selected based on the belief that the mutant would not be so invasive as to take over the immune system, causing stress and predisposing the bird to other infectious agents.

D. Morphological and biochemical characteristics of the mutant and parent non-mutant strains. Colony morphology and hemolytic characteristics of the mutant and parent non-mutant *E. coli* were determined on blood agar plates, incubated at appropriate temperatures for a period of 24 hours.

To determine if any biochemical differences existed between the mutant and parent non-mutant, biochemical testing was done at 32° C. (mutant) and 41° C. (non-mutant). Biochemical reactions were recorded positive or negative after 24 hours of incubation (see Table 3 below).

TABLE 3

BIOCHEMICAL CHARACTERISTIC'S OF THE MUTANT AND NON-MUTANT *E. COLI*

| TEST | MUTANT | NON-MUTANT |
|---|---|---|
| ARGNINE DIHYDROLASE | − | − |
| LYSINE DECAPSOXYLASE | + | + |
| ORNITHINE DECARBOXYLASE | + | + |
| CITRATE | − | − |
| HYDROGEN SULFIDE | − | − |
| UREA HYDROLYSIS | − | − |
| TRYPTOPHANE DEAMINASE | − | − |
| O-NITROPHENYL-B-d-GALACTOSE | + | + |
| NIDOLE | + | + |
| VOGES-PROSKALER | − | − |
| GELATIN HYDROLYSIS | − | − |
| GLUCOSE | + | + |
| ACID | + | + |
| GAS | + | + |
| LACTOSE | + | + |
| MANNITOL | + | + |
| NOSITOL | − | − |
| SORBITOL | + | + |
| RHAMNOSE | + | + |
| SUCROSE | − | − |
| MELBIOSE | + | + |
| AMYGOALIN | − | − |
| ARABNOSE | + | + |
| OXIDASE | − | − |
| MOTILITY | + | + |
| HEMOLYSIS | − | − |

KEY
+ POSITIVE WITHIN 24 HR INCUBATION
− NO REACTION

As seen in Table 3, there was no difference in morphological and biochemical properties between the mutant and parent non-mutant *E. coli* as demonstrated from the various biochemicals tested.

Colonies of the mutant and parent non-mutant appeared smooth with entire margins, showing no hemolysis when grown on blood agar plates. The only morphological difference seen between the mutant and non-mutant was the smaller colony size of the mutant, probably due to the slower growth rate of the mutant strain.

E. Test for pathogenicity. To determine if the mutant was pathogenic to turkeys, 16-week old turkeys were equally divided into two groups. Both groups were exposed intravenously with 1 ml of either the mutant or parent non-mutant culture whose pathogenicity to turkeys was established in our laboratory at a concentration of $10^9$ CFU/ml in saline. Pathogenicity was determined by the time of death of birds in both groups. Birds found dead during the period of observation were necropsied and bacteriological examination of the heart, liver and hock joints was done.

The pathogenicity of the mutant was compared to parent virulent non-mutant strain 078, as indicated in Table 4 below. All birds given the virulent 078 died within one week post exposure. No deaths were seen with the infected mutant group. All dead birds of the virulent group were necropsied at the time of death and examined for gross signs of infection. *E. coli* was isolated from the heart, liver and hock joints from all birds infected with the virulent strain. All birds appeared healthy in the mutant group and were necropsied one week post-exposure. There were no signs of infection and all cultures were negative for *E. coli*.

Figure 1:
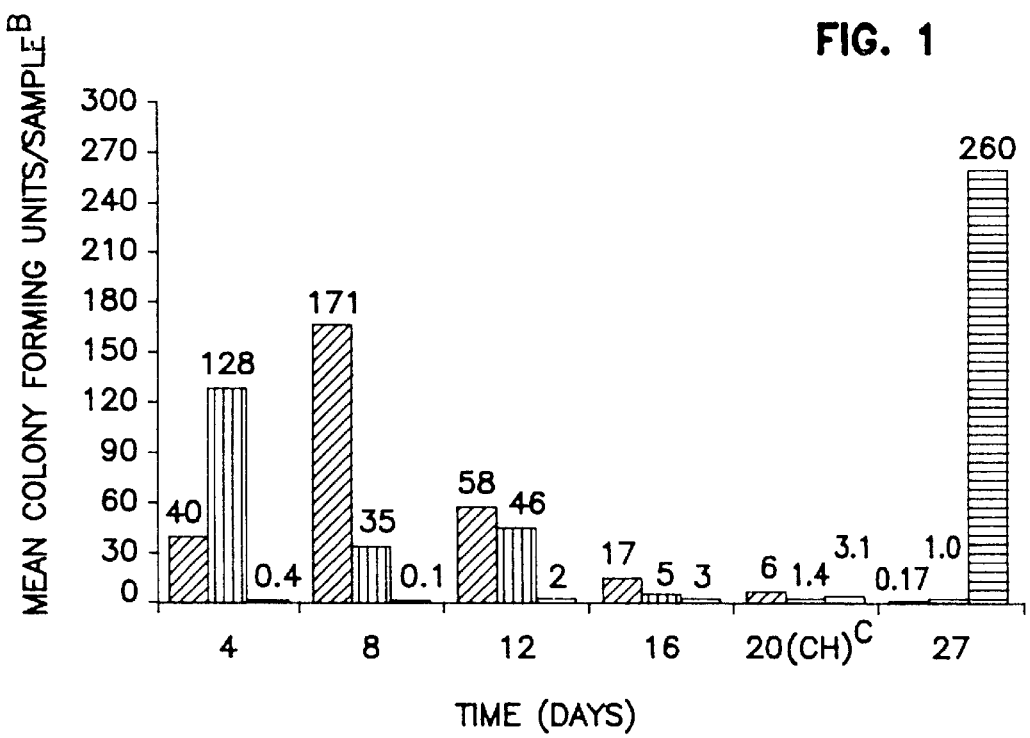
FIG. 1 is a graphic description of nasal colonization of temperature sensitive mutant, non-mutant E. coli 078 and control (non-vaccinated/challenged). The mutant and non-mutant groups were intranasally inoculated at two weeks of age. The control was non-inoculated/challenged. Each sampling time represents the mean colony forming units/group taken intranasally at four-day intervals. Twenty days post inoculation, all groups were challenged intranasally with $2\times10^6$ CFU/bird with a nalidixic acid resistant strain of *E. coli* 078

The degree of colonization of the trachea and nasal mucosa of the mutant, non-mutant and control (non-vaccinated/challenged) are summarized in FIGS. 1 and 2. Extensive colonization of the nasal mucosa was seen with the mutant strain, with slight colonization of the lower trachea. The non-mutant colonized both the nasal and tracheal mucosa, with greater affinity for the lower trachea. Four days post-vaccination, colonization of the nasal mucosa with the mutant was significantly lower than with the non-mutant, possibly due to the slower growth rate of the mutant. Colonization with the mutant in the nasal mucosa

TABLE 4

ISOLATION OF MUTANT AND NON-MUTANT *E. COLI* FROM THE LIVER, HEART, AND HOCK JOINT.[A]

| | ISOLATION OF MUTANT *E. COLI*[C] BIRDS NECROPSIED AT 7 DAYS POST INOCULATION | | | | ISOLATION OF NON-MUTANT *E. COLI*[B] AT TIME OF DEATH | | | |
|---|---|---|---|---|---|---|---|---|
| BIRD | DEAD | LIVER | HEART | HOCK | DEAD | LIVER | HEART | HOCK |
| 1 | 0 | 0 | 0 | 0 | 24 hr | + | + | + |
| 2 | 0 | 0 | 0 | 0 | 24 hr | + | + | + |
| 3 | 0 | 0 | 0 | 0 | 48 hr | + | + | + |
| 5 | 0 | 0 | 0 | 0 | 48 hr | + | + | + |
| 6 | 0 | 0 | 0 | 0 | 72 hr | + | + | + |
| 7 | 0 | 0 | 0 | 0 | 96 hr | + | + | + |
| 8 | 0 | 0 | 0 | 0 | 96 hr | + | + | + |

[A]THE MUTANT AND NON-MUTANT GROUPS WERE INTRAVENOUSLY INOCULATED WITH $1 \times 10^9$ COLONY FORMING UNITS/BIRD.
[B]SAMPLES FROM THE NON-MUTANT GROUP WERE TAKEN AT TIME OF DEATH.
[C]SAMPLES FROM THE MUTANT GROUP WERE TAKEN 7 DAYS POST INOCULATION.

F. Vaccination. Sixty turkeys from a commercial hatchery were raised in isolation from one day of age. At two weeks of age, birds were equally divided into three groups. Each group of birds was housed separately in an isolation facility. In group 1, the mutant was inoculated intranasally into 20 two-week old turkeys. Each bird received 0.1 ml saline containing $10^7$ CFU/ml.

G. Nasal and tracheal colonization. Swabs were taken from the internal nares through the palatine cleft and from the lower trachea prior to exposure from all birds to ascertain pre-exposure status. Samples were taken from all birds at 4-day intervals post exposure to examine the degree of colonization of the mutant strain compared with the virulent strain. The second group was intranasally inoculated with the virulent 078 of equal concentration ($10^7$ CFU/ml). Twenty birds in group 3 were used as uninoculated controls. Swabs were streaked directly onto EMB agar plates and incubated at 32° C. and 41° C. for 48 hours. The mutant strain was identified by its impaired growth at 41° C. compared to its growth at 32° C.

increased dramatically 8 days post vaccination and remained at a higher level than with the non-mutant up to the period of challenge. Slight colonization with the mutant was seen in the trachea but was not much greater than with the control.

The non-mutant extensively colonized both the nasal and tracheal mucosa but the degree of colonization predominated in the lower trachea. Colonization of the mutant and non-mutant in the nasal and tracheal mucosa lasted 3 weeks.

H. Challenge studies. Twenty days post exposure to the mutant and parent virulent non-mutant strain of *E. coli*, turkeys in all three groups were challenged intranasally with a Nalidixic acid resistant virulent strain of *E. coli* 078. Each bird was inoculated with 0.2 ml of saline containing $10^7$ CFU/ml. Seven days post-challenge, swabs were taken from the internal nares and lower trachea from all birds in each group. Swabs were then streaked onto MacConkey agar plates containing 100 )g/ml Nalidixic acid incubated at 32° C. and 41° C. for 48 hours, as indicated in Table 5 below.

TABLE 5

NASAL AND TRACHEAL COLONY FORMING UNITS IN MUTANT, NON-MUTANT AND CONTROL GROUPS 7 DAYS POST CHALLENGE[A]

| Nasal[B] | | | Tracheal[B] | | |
|---|---|---|---|---|---|
| Mutant | Non mutant | Control | Mutant | Non mutant | Control |
| 0 | 0 | >300 | 0 | 79 | >300 |
| 0 | 3 | >300 | 0 | 4 | >300 |
| 0 | 2 | 296 | 0 | 0 | >300 |
| 0 | 1 | >300 | 0 | 5 | 157 |
| 0 | 0 | 194 | 2 | 1 | 190 |
| 2 | 0 | 169 | 0 | 150 | 135 |
| 0 | 3 | >300 | 0 | 0 | >300 |
| 0 | 2 | 219 | 0 | 49 | 174 |
| 0 | 1 | | 0 | | |
| 0 | 0 | | 0 | | |
| 0 | 0 | | 0 | | |
| 0 | 0 | | 0 | | |
| 0.17 | 1.0 | 260 $\bar{x}$ CFU[C] | 0.16 | 36.0 | 232.0 $\bar{x}$ CFU[C] |

[A]TWENTY DAYS POST INOCULATION ALL GROUPS WERE INTRANASALLY CHALLENGED WITH $2 \times 10^6$ CFU/BIRD WITH A NALIDIXIC ACID RESISTANT STRAIN OF *E. COLI* 073.
[B]SAMPLES WERE TAKEN INTRANASALLY AND INTRATRACHEALLY 7 DAYS POST CHALLENGE.
[C]$\bar{x}$ CFU = MEAN COLONY FORMING UNITS.

Challenge was 20 days post vaccination with a virulent 078 Nalidixic acid resistant *E. coli* (FIGS. 1 and 2). Seven days post challenge, slight nasal and tracheal colonization was detected in the mutant group.

The non-mutant group had slight nasal colonization with moderate colonization of the lower trachea. The unexposed control group had extensive colonization of the nasal and lower trachea. No signs of infection were seen in any of the exposed birds. Both vaccinated groups prevented the colonization of the virulent *E. coli* 078 challenge.

Table 6 below is a summary of FIGS. 1 and 2, but is expressed in mean cumulative colony forming units in the trachea and nasal passages. Mean colony forming units were calculated from day 4 through day 27 to compare the pre-challenge and post-challenge of the mutant, non-mutant and control (non-vaccinated challenged).

TABLE 6

MEAN CUMULATIVE COLONY FORMING UNITS IN THE TRACHEA AND NASAL PASSAGES

| | PRE-CHALLENGE[A] | | POST-CHALLENGE[B] | |
|---|---|---|---|---|
| TREATMENT | NASAL | TRACHEA | NASAL | TRACHEA |
| TS-MUTANT | 48.87 | 5.78 | 0.17 | 0.16 |
| NON-MUTANT | 8.33 | 78.44 | 1.0 | 36.0 |
| NONE | 1.84 | 1.44 | 260 | 232 |

[A]MEAN CUMULATIVE COLONY FORMING UNITS OF THE MUTANT, NON-MUTANT AND CONTROL GROUPS OF THE PRE-CHALLENGE PERIOD (DAYS 4–20)
[B]MEAN CUMULATIVE COLONY FORMING UNITS OF THE MUTANT, NON-MUTANT AND CONTROL GROUPS OF THE POST CHALLENGE PERIOD (DAYS 20–27)

EXAMPLE 2

Live Mutant Ola *E. coli* Vaccine

Preparation and Evaluation of Efficacy in Chickens

A. Bacteria Mutant *E. coli* Vaccine—*E. coli* 01a/MP MSB 120189. Frozen titer: 1×$10^9$ CFU/ml.

B. Chickens—SPF leghorns, HY-VAC Hatcheries, Adel, Iowa. The chicks were received at [one ?] day of age and reared in isolation until used for testing at 3 weeks of age.

C. *E. coli* Challenge—Virulent *E. coli* 01a/V 042990 and *E. coli* 078/V 120789 Frozen stocks. Titers: 01a/V=3.6×$10^9$ CFU/ml and 078/V=1.6×$10^9$ CFU/ml.

At 3 weeks, chickens were stressed by eyedrop inoculation with virulent B-41 strain IBV and by sinus infection with virulent R strain MG culture. Seven days later, birds were injected transnasally with virulent *E. coli* via the nares or through the palatine cleft. Seven days later, birds were sacrificed and examined for air sac lesions, pericarditis, liver lesions, diarrhea and general condition. To aid in evaluating results, signs were scored for increasing severity: 1=normal; 2=air sacs cloudy only; 3=one air sac showing lesions; 4=both air sacs showing lesions; 5=pericarditis, liver lesion, diarrhea; 6=death.

D. Challenge Study—Chickens in separate groups were vaccinated intranasally (IN) with graded dosages of $10^5$, $10^6$, and $10^7$ CFU/bird of *E. coli* vaccine. At 3 weeks, vaccinated and control groups were divided equally, stressed and challenged with 01a/V or 078/V as described.

1. 01a/V challenge—no test. The challenge was unable to bring down any of the unvaccinated controls.
2. 078/V challenge—As indicated in Table 7 below, the 01a/MP vaccine provided significant protection against 078/V challenge at all three dosage levels when lesion score indices were compared. The 01a/MP vaccine provided significant protection at $10^6$ and $10^7$ dosage levels when groups were evaluated for total birds remaining normal.

TABLE 7

Efficacy of Live Mutant 01A *E. coli* Vaccine in Leghorn Chickens Challenged Intranasally with Virulent *E. coli* 078 at 4 weeks Postvaccination

| Intranasal Dosage (1) (CFU/Bird) | Lesion Score (2) (No. Birds) | | | | | | Mean | Birds Protected (3) |
|---|---|---|---|---|---|---|---|---|
| | 1 | 2 | 3 | 4 | 5 | 6 | | |
| | (negative) | | | | (most severe) | | | |
| $10^7$ | 10 | 6 | 2 | 0 | 2 | 0 | $1.9^a$ | $10/20^{aa}$ |
| $10^6$ | 14 | 0 | 0 | 0 | 6 | 0 | $2.2^a$ | $14/20^{aa}$ |
| $10^5$ | 8 | 4 | 0 | 2 | 6 | 0 | $2.8^a$ | $8/20^{bb}$ |
| Controls | 1 | 5 | 2 | 1 | 3 | 8 | $4.2^b$ | $1/20^{bb}$ |

(1) Birds vaccinated at 3 weeks by IN route.
(2) Birds stressed at 3 weeks PV with IBV and MG and then challenged 7 days later with virulent *E. coli*. Necropsied 7 days later. See text for lesion score schedule.
(3) Mean, "a" significantly different than "b". Groups labelled "aa" significantly different than "bb" groups.

EXAMPLE 3

Live Mutant 078 *E. coli* Vaccine

Preparation and Evaluation of Efficacy in Chickens

A. Bacterial Mutant *E. coli* Vaccine—*E. coli* 078. Frozen.

B. Chickens—SPF leghorns, HY-VAC Hatcheries, Adel, Iowa. The chicks were received at one day of age and reared in isolation until used in testing at about 3 weeks of age.

C. *E. coli* Challenge—Virulent E. coli 078. Frozen. Titer: $1.6 \times 10^9$ CFU/ml. A volume of 0.1 ml was injected into the nasal tract via the nares or the palatine cleft or infectious bronchitis virus IBV/MG-stressed birds.

D. Challenge Study

Trial 1—Chickens were vaccinated intranasally with $10^6$ CFU of *E. coli* vaccine. At 3 weeks, the vaccinates and controls were stressed by eye drop inoculation of virulent B-41 bronchitis virus and by sinus injection with the virulent "R" strain *Mycoplasma fallisepticum*. Seven days later, the birds were challenged intranasally with virulent *E. coli*. After another 7 days the birds were sacrificed and examined for 1) air sac lesions, 2) pericarditis, 3) liver lesions, 4) diarrhea, and 5) general condition. To aid in evaluating results, signs were scored for increasing severity.

1=normal
2=air sacs cloudy
3=one air sac showing lesions
4=both air sacs showing lesions
5=pericarditis, liver lesions
6=death Additional birds were necropsied at 14 and 21 days after prechallenge stress.

Trial 2—Chickens were vaccinated with graded dosages of *E. coli* vaccine and then challenged by same methods as Trial 1.

Trial 1 Results (Table 8) at necropsy at 7 days show significant reduction of challenge signs in vaccinated birds. This group showed an index of 2.6 vs. 4.7 for nonvaccinated controls. Further, 10/20 vaccinates remained normal vs. 1/20 controls. Both measurements were significantly different.

Necropsy of additional birds showed rapid clearing of signs at 14 and 21 days. only 1 vaccinate vs. 4 controls showed signs at this time. At 21 days, all birds were negative for air sac signs.

Trial 2 Results (Table 9) showed significant reduction in challenge signs at $10^6$ and $10^7$ CFU dosage levels. These birds showed indices of 2.2 and 2.4 vs. 3.8 for the control group. Similarly, 8/20 and 7/20 vaccinates in these groups remained free of challenge signs vs. only 1/14 controls. An additional group of vaccinates receiving $10^5$ CFU did not show significant protection. An index of 2.9 and only 3/20 negative birds in this group was not significantly different than the controls.

As indicated in Tables 8 and 9, mutant *E. coli* vaccine 078 in two trials produced significant protection against virulent *E. coli* challenge administered by respiratory route. Protection was seen as a reduction in air sac and other lesions after challenge. They were best evaluated at 7 days since they disappeared rapidly thereafter, being gone at 21 days. Preferred dosages for protection should be at least $10^6$ CFU.

TABLE 8

TRIAL 1. Preliminary Vaccination-Challenge Trial With Live Mutant 078 *E. coli* Vaccine in Chickens. Intranasal Challenge With Virulent *E. coli* 078

| Vaccine Dosage (1) (CFU/Bird) | Lesion Score (2) (No. Birds) | | | | | | Mean | Birds Protected |
|---|---|---|---|---|---|---|---|---|
| | 1 | 2 | 3 | 4 | 5 | 6 | | |
| | (negative) | | | | (most severe) | | | |
| 7 Days Postchallenge | | | | | | | | |
| $10^6$ | 10 | 6 | 1 | 0 | 4 | 1 | 2.6 | 10/20 |
| Controls | 1 | 5 | 2 | 1 | 3 | 8 | 4.7 | 1/20 |
| 14 Day Postchallenge | | | | | | | | |
| $10^6$ | 19 | 1 | 0 | 0 | 0 | 0 | 1.1 | 19/20 |
| Controls | 16 | 4 | 0 | 0 | 0 | 0 | 1.2 | 16/20 |
| 21 Days Postchallenge | | | | | | | | |
| $10^6$ | 10 | 0 | 0 | 0 | 0 | 0 | 1.0 | 10/10 |
| Controls | 10 | 0 | 0 | 0 | 0 | 0 | 1.0 | 10/10 |

(1) Birds stressed by eyedrop inoculation with B-41 IBV and intrasinus injection of "R" Strain MG at 7 days before challenge.
(2) Increasing severity of challenge reaction at necropsy.

TABLE 9

TRIAL 2. Efficacy of Live Mutant 078 *E. coli* Vaccine in Leghorn Chickens Challenged Intranasally With Virulent *E. coli* 078 at 4 Weeks Postvaccination

| Intranasal Vaccine Dosage (CFU/Dose) | Lesion Score (2) (No. Birds) | | | | | | Mean | Birds Protected |
|---|---|---|---|---|---|---|---|---|
| | 1 | 2 | 3 | 4 | 5 | 6 | | |
| | (negative) | | | | (most severe) | | | |
| $10^5$ | 3 | 6 | 4 | 4 | 3 | 0 | 2.9 | 3/20 |
| $10^6$ | 8 | 6 | 3 | 1 | 2 | 0 | 2.2 | 8/20 |
| $10^7$ | 7 | 7 | 0 | 3 | 3 | 0 | 2.4 | 7/20 |
| Controls | 1 | 1 | 5 | 3 | 1 | 3 | 3.8 | 1/14 |

(1) Birds stressed by eyedrop inoculation with B-41 IBV and intrasinus injection of "R" Strain MG at 7 days before challenge.
(2) Increasing severity of challenge reaction at necropsy.

What is claimed is:

1. A method for obtaining a stable temperature sensitive mutant of *Escherichia coli* capable of colonizing the nasal mucosa and enhancing immunologic resistance to colibacillosis in domestic fowl, comprising the steps of:

(a) treating a culture of *Escherichia coli* with a mutagen and a protein synthesis inhibitor, said mutagen and protein synthesis inhibitor being employed in an amount sufficient to maximize mutation and minimize reversion frequency;
(i) said mutagen selected from the group consisting of N-methyl-N-nitro-N-nitrosoguanidine (MNNG), ethyl methane sulfonate (EMS), and nitrous oxide;
(ii) said protein synthesis inhibitor selected from the group consisting of chloramphenicol, actinomycin, spectinomycin, linocmycin and erythromycin;

b) selecting said culture mutants exhibiting growth at 32° C. but not at 41° C. and having a reversion frequency of less than $1 \times 10^{-8}$.

2. The method of claim 1 wherein said protein synthesis inhibitor is chloramphenicol.

3. The method of claim 1 wherein said culture is treated with about 25 µg/ml chloramphenicol.

\* \* \* \* \*

UNITED STATES PATENT AND TRADEMARK OFFICE
CERTIFICATE OF CORRECTION

PATENT NO.   : 6,077,516
DATED        : June 20, 2000
INVENTOR(S)  : Nagaraja et al.

It is certified that error appears in the above-identified patent and that said Letters Patent is hereby corrected as shown below:

Column 1,
Line 8-9, "E. colivaccine" should read -- E. coli vaccine --

Column 2,
Line 39, "Microbic" should read -- Microbio --

Column 10,
Line 56, "100)g/ml" should read -- 100ug/ml --

Column 11,
Line 3, (footnote), Table 5: "073" should read -- 078 --

Signed and Sealed this

Twenty-third Day of October, 2001

*Attest:*

NICHOLAS P. GODICI
*Attesting Officer*    Acting Director of the United States Patent and Trademark Office